United States Patent
Slionski

(10) Patent No.: US 6,390,094 B1
(45) Date of Patent: May 21, 2002

(54) DEVICE OF REGULATING AIR FLOW THROUGH AN ENDOTRACHEAL TUBE

(76) Inventor: Henry Slionski, 36 Crescent Pl., Smithtown, NY (US) 11787

( * ) Notice: Subject to any disclaimer, the term of this patent is extended or adjusted under 35 U.S.C. 154(b) by 0 days.

(21) Appl. No.: 09/165,281

(22) Filed: Oct. 2, 1998

(51) Int. Cl.$^7$ .............................................. A61M 16/00
(52) U.S. Cl. ............................... 128/207.16; 128/207.14
(58) Field of Search ...................... 128/207.14–207.18, 128/200.24, 201.28, 203.12, 204.18, 205.24, 207.12

(56) References Cited

U.S. PATENT DOCUMENTS

| | | |
|---|---|---|
| 2,804,076 A | 8/1957 | Giraudon |
| 3,066,674 A | 12/1962 | Capra |
| 3,683,931 A | 8/1972 | Chelucci et al. |
| 3,844,290 A | 10/1974 | Birch et al. |
| 3,924,637 A | 12/1975 | Swanson |
| 3,952,335 A | 4/1976 | Sorce et al. |
| 4,015,608 A | 4/1977 | Rogers |
| 4,040,428 A | 8/1977 | Clifford |
| 4,202,330 A | 5/1980 | Jariabka ................ 128/204.18 |
| 4,325,366 A | 4/1982 | Tabor .................... 128/207.16 |
| 4,494,252 A | 1/1985 | Chaoui |
| 4,538,607 A | 9/1985 | Saul ....................... 128/207.16 |
| 4,582,058 A | 4/1986 | Depel et al. ........... 128/207.17 |
| 4,627,433 A | 12/1986 | Lieberman ............. 128/207.16 |
| 4,646,733 A | 3/1987 | Stroh et al. ............ 128/207.16 |
| 4,739,987 A * | 4/1988 | Nicholson .............. 128/207.16 |
| 4,809,693 A | 3/1989 | Rangoni et al. ....... 128/207.16 |
| 4,852,565 A | 8/1989 | Eisele .................... 128/207.14 |
| 4,877,025 A | 10/1989 | Hanson .................. 128/207.16 |
| 5,048,518 A | 9/1991 | Eliachar et al. ........ 128/207.14 |
| 5,059,208 A | 10/1991 | Coe et al. |
| 5,107,828 A | 4/1992 | Koss et al. ............. 128/200.26 |
| 5,123,922 A | 6/1992 | Berg |
| 5,146,916 A | 9/1992 | Catalani ................ 128/207.14 |
| 5,313,939 A | 5/1994 | Gonzalez ............... 128/207.14 |
| 5,392,775 A * | 2/1995 | Adkins et al. ......... 128/207.16 |
| 5,445,145 A | 8/1995 | Redmon ................. 128/207.16 |
| 5,505,198 A | 4/1996 | Siebens et al. ........ 128/207.16 |
| 5,538,002 A | 7/1996 | Boussignac et al. ... 128/207.16 |
| 5,605,149 A | 2/1997 | Warters ................. 128/207.14 |
| 5,647,355 A | 7/1997 | Starr et al. ............. 128/205.24 |
| 5,738,095 A | 4/1998 | Persson ................. 128/207.14 |

* cited by examiner

*Primary Examiner*—Glenn K. Dawson
(74) *Attorney, Agent, or Firm*—Kenyon & Kenyon

(57) ABSTRACT

An endotracheal tube flow control device includes a hollow tubular member, a selectively adjustable surface, and an endotracheal tube. The proximal end of the tubular member is connected to the endotracheal tube. The selectively adjustable surface is connected to the distal end of the tubular member. By selecting the position of the adjustable surface, the area of the air flow opening of the tubular member can be increased or decreased. The endotracheal tube flow control device allows a patient to control breathing by selectively adjusting the breathing area of the endotracheal tube.

16 Claims, 8 Drawing Sheets

DEVICE OF REGULATING AIR FLOW THROUGH AN ENDOTRACHEAL TUBE

FIELD OF THE INVENTION

The present invention relates to devices for use with an endotracheal tube, and in particular to a selectively adjustable device for regulating air flow through an endotracheal tube.

BACKGROUND INFORMATION

Intubation involves the insertion of a conduit into the trachea of a patient. One of the most commonly used conduits is an endotracheal, tracheotomy, or similar tube (herein collectively referred to as endotracheal tubes). For intubation, the proximal end of the endotracheal tube is extended into the trachea of a patient and the distal end protrudes from the patient's neck. The patient may then breathe through the tube. However, patients often find it difficult to control their breathing through an endotracheal tube. The functions performed by the mouth and nose in regulating the flow of air to the lungs are not provided for in a standard endotracheal tube which often has a constant cross-sectional area and therefore allows a constant flow of air.

Devices have been created to allow a patient to control their breathing through an endotracheal tube, but these have shortcomings. For example, some devices only allow a patient to select an open or closed position of the distal opening of the endotracheal tube. Patients find these devices inadequate when they wish to decrease their breathing but not to discontinue breathing through the endotracheal tube. Other devices are complicated or awkward, and may be prone to malfunction. Still other devices may be large and unwieldy, and thus may restrict movement or cause embarrassment by calling unnecessary attention to the patient's physical condition.

SUMMARY OF THE INVENTION

The present invention provides an endotracheal tube flow control device, which includes a hollow longitudinal member and a selectively adjustable valve mechanism. One end of the longitudinal member may be connected to an endotracheal tube. The selectively adjustable valve mechanism is connected to a second end of the longitudinal member. By selecting the position of the adjustable valve mechanism, the air flow through the longitudinal member can be gradually increased or decreased. The endotracheal tube flow control device allows a patient to control breathing by selectively adjusting the breathing area of the endotracheal tube.

DETAILED DESCRIPTION OF THE INVENTION

Figure 1:
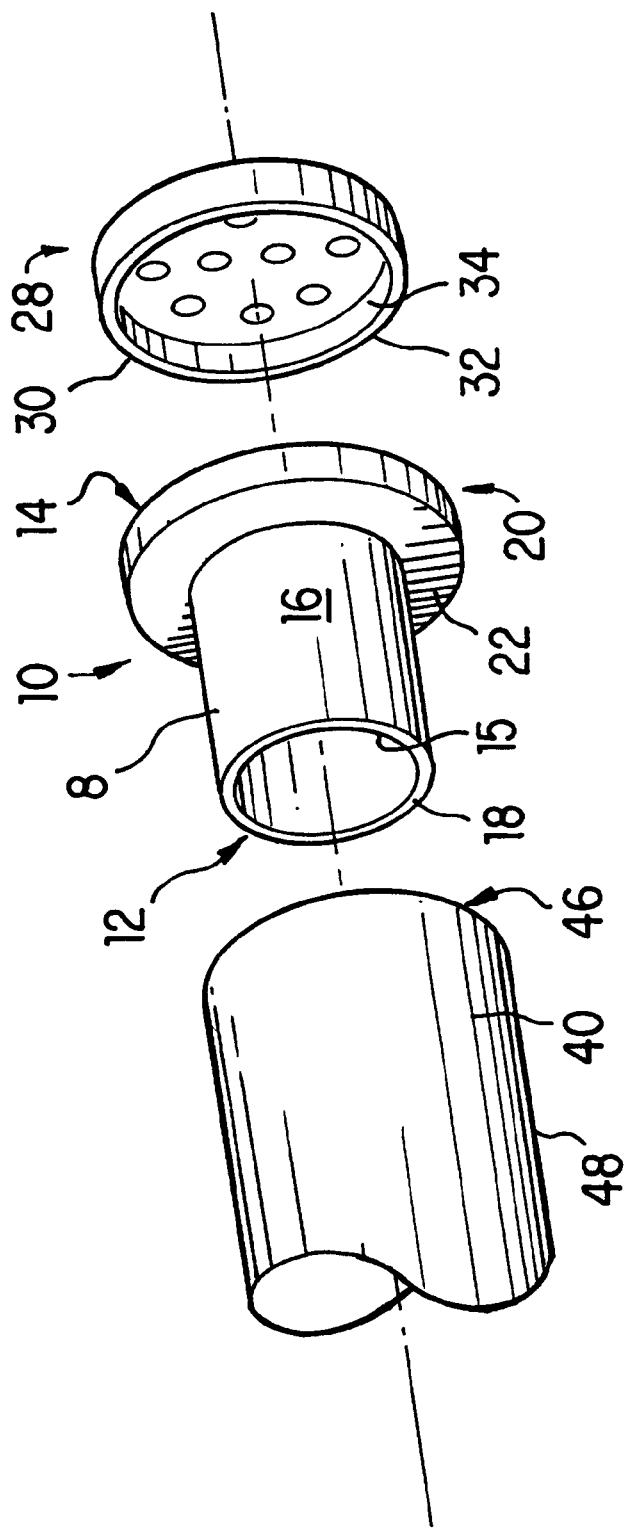
FIG. 1 is an assembly diagram of an exemplary endotracheal tube flow control device according to the present invention.

FIG. 1 illustrates a flow control device 8 according to the present invention which includes a longitudinal member 10, and a valve mechanism that is selectively and gradually positionable between a fully open position and a fully closed position. Flow control device 8 may include an air conduit 40 such as an endotracheal tube or a connecting element for an endotracheal tube. In general, the valve mechanism is capable of continual adjustment between a fully open position and a fully closed position, so that the user can receive a desired flow of air. Gradual actuation of the valve towards the fully open position gradually increases the flow of air, while gradual actuation towards the fully closed position gradually reduces the flow of air.

Longitudinal member 10 preferably includes a longitudinal bore 15, a proximal end 12, a distal end 14, an outside surface 16 and an inside surface 18. Preferably, longitudinal member 10 is tubular with a circular cross section, although any suitable geometry of longitudinal member could be used. In use, longitudinal member 10 connects air conduit 40 with the valve mechanism, and so in general longitudinal member 10 should be shaped to allow a flow of air and to support a selectively and gradually adjustable valve mechanism. Preferably longitudinal member 10 is constructed of a rigid or semi-rigid plastic but could alternatively be constructed of any suitable material.

Figure 2:
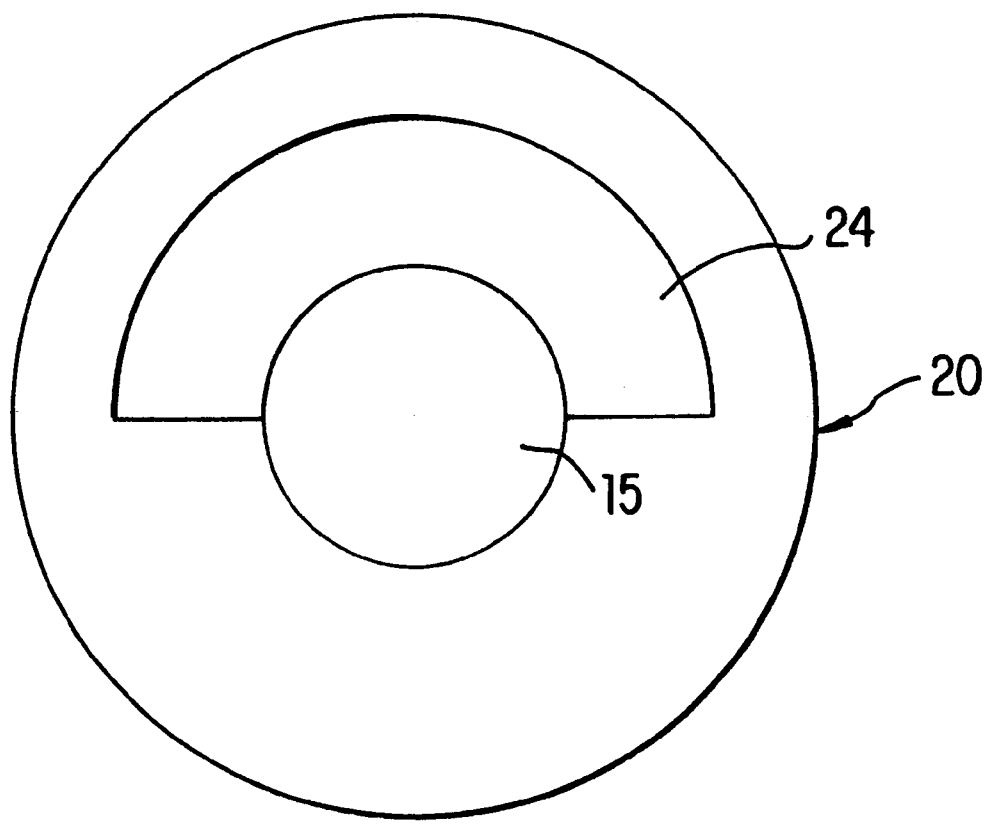
FIG. 2 is a front view of a longitudinal member of the flow control device of FIG. 1.

In the exemplary embodiment illustrated in FIG. 1, longitudinal member 10 includes a flange 20. Flange 20 includes a proximal flange surface 22, a distal flange surface 26, and a recess 14, which is preferably semi-circular as illustrated in FIG. 2. As discussed below, recess 14 cooperates with an end cap 28 to form the valve mechanism of this embodiment. Flange 20 extends radially outward from the distal end 14 of longitudinal member 10, providing a shoulder which may abut the distal surface 46 of the air conduit 40 when longitudinal member 10 and air conduit 40 are joined.

Recess 24 may be disposed on the distal end 26 of flange 20. In the illustrated embodiment material has been removed concentrically outward on one side of the distal surface 26 of flange 20. Preferably recess 24 does not extend to the outer edge of flange 20. This preferred geometry is best illustrated in FIG. 2. In general, recess 24 provides a selectively available breathing passage to end cap 28, as discussed below, and so may be shaped in any matter suitable for this purpose.

Figure 3:
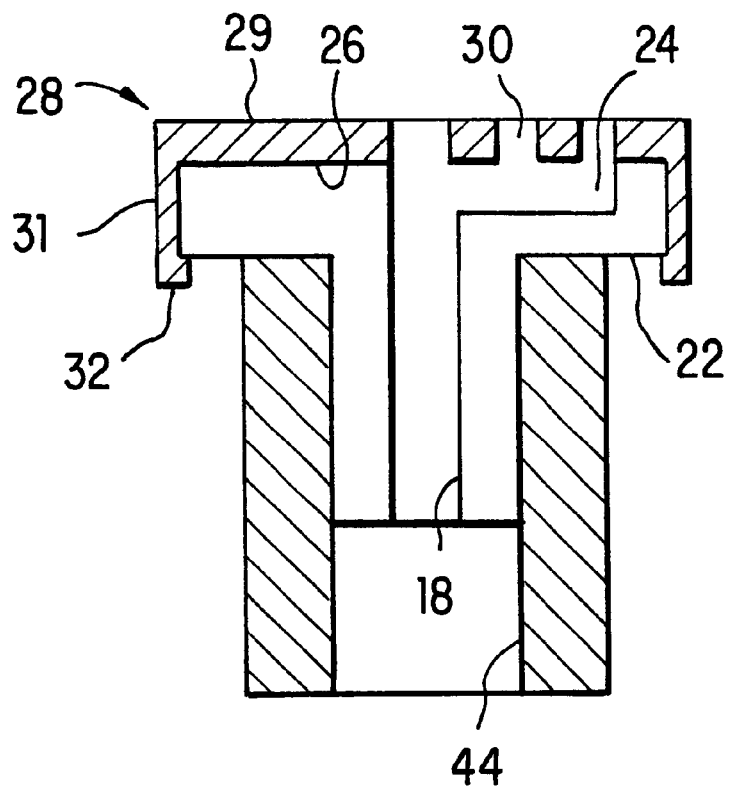
FIG. 3 is a cross-sectional side view of the flow control device of FIG. 1.
Figure 4:
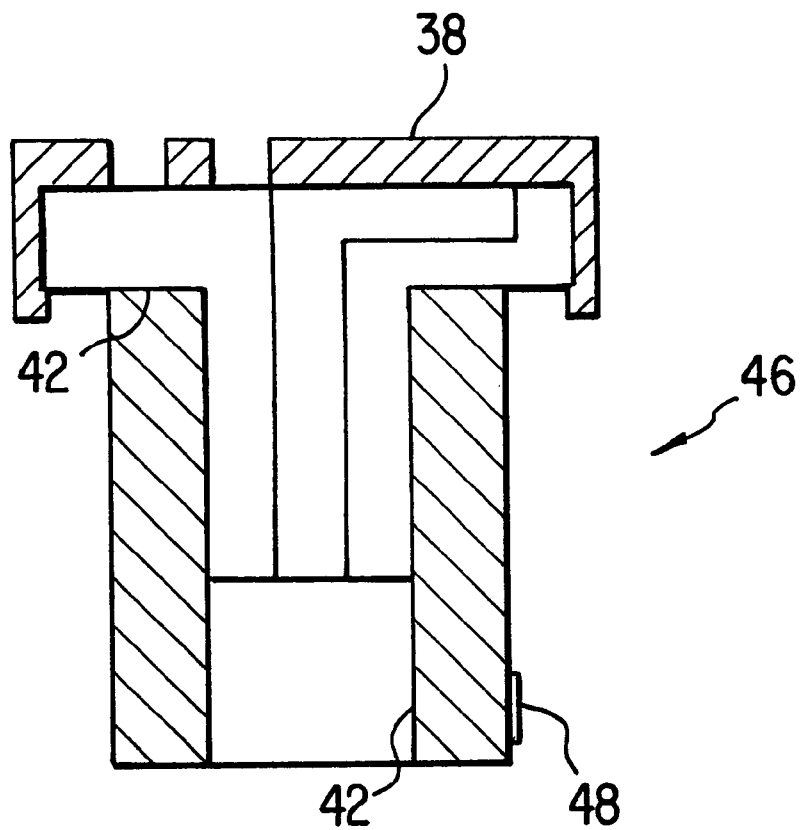
FIG. 4 is a second cross-sectional side view of the flow control device of FIG. 1.

In an exemplary embodiment end cap 28 includes an end face 29 having at least one aperture 30 therethrough, a depending skirt 31, and a lip 32. Preferably a plurality of apertures 30 are provided, and these are preferably grouped toward one side of end face 29. This placement allows the rotation of end cap 28 to provide a range of selectable breathing areas between a fully open position (see FIG. 3) and a fully closed position (see FIG. 4). As end cap 28 is gradually rotated, for example, towards the fully open position, air flow through device 8 gradually increases. While the exemplary embodiment contains multiple apertures 30, a single aperture 30 could also be provided.

Skirt 31 may depend from end face 29. Preferably, an inner diameter of skirt 31 is slightly larger than an outer diameter of flange 20. This allows end cap 28 to rotate concentrically around the outside of flange 20. At a proximal edge of skirt 31 is a lip 32 protruding concentrically inward. Lip 32 may have a smaller inner diameter than the outer diameter of flange 20, thereby allowing end cap 28 to remain secured on flange 20 in, for example, a snap-fit relationship. Preferably end cap 28 is made from a hard plastic that is adequately rigid and smooth to allow easy rotation of the cap yet is also adequately flexible to allow for snap-fitting to flange 20.

As noted above, air conduit 40 may be integral with an endotracheal tube or could be constructed for connection to an existing endotracheal tube. The distal end 46 of air conduit 40 is coupled to the proximal end 12 of longitudinal member 10. In particular, the inner surface of conduit 40 preferably fits in frictional interference with the outside surface 16 of longitudinal member 10, with the distal surface 46 of conduit 40 abutting the proximal surface 22 of flange 20. In this embodiment, air conduit 40 engages the outside surface 16 of longitudinal member 10. In an alternative assembly, however, air conduit 40 could fit inside longitudinal member 10. This coupling could likewise be achieved with frictional interference, which generally allows easy separation for cleaning or other purposes, but any suitable connection may be employed.

Figure 5:
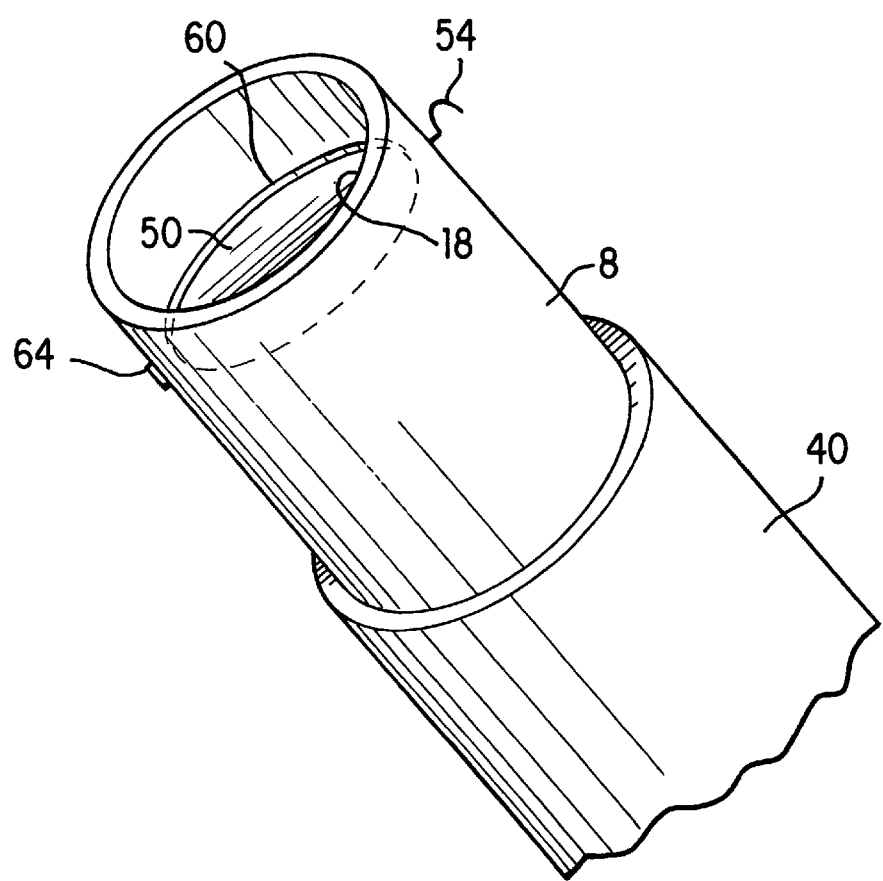
FIG. 5 is a top view of a second exemplary endotracheal tube flow control device according to the present invention.
Figure 6:
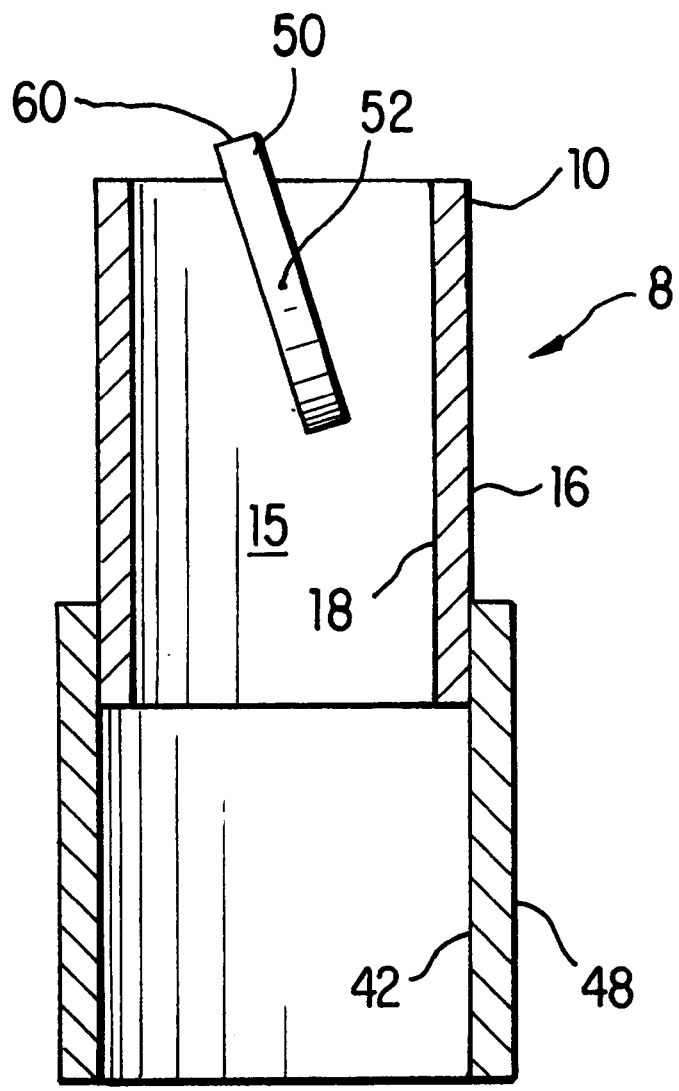
FIG. 6 is a cross-sectional side view of the flow control device of FIG. 5.
Figure 7:
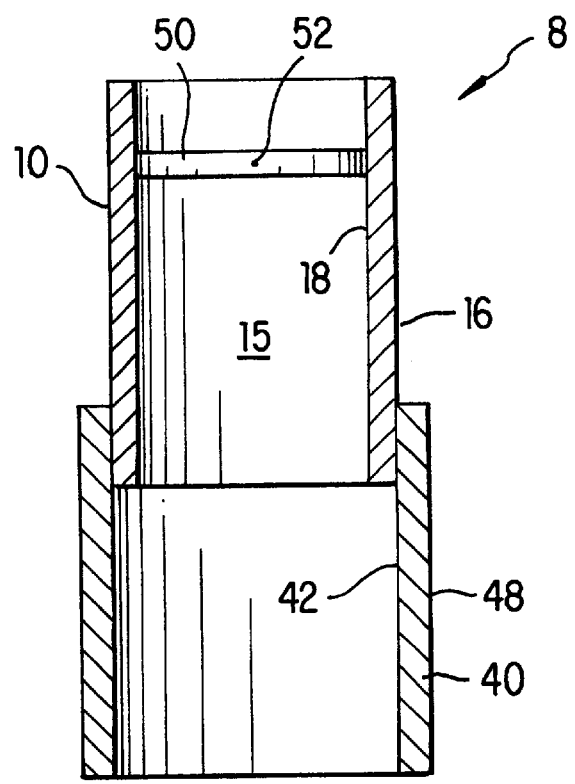
FIG. 7 is a second cross-sectional side view of the flow control device of FIG. 5.

FIG. 5 illustrates a second exemplary embodiment of a device 8 according to the present invention, in which the valve mechanism takes the general form of a throttle or butterfly valve. In this embodiment, longitudinal member 10 includes a valve plate 50 which is pivotable between a fully open position (see FIG. 6) and a fully closed position (see FIG. 7). Valve plate 50 is preferably a thin disk with an outer edge 60 which contacts the inside surface 18 of longitudinal member 10 when valve plate 50 is in the fully closed position. Alternatively, valve plate 50 could take any shape suitable to selectively and gradually pivot between a fully open position that allows the free flow of air and a fully closed position which minimizes the flow of air.

When in the fully open position, valve plate 50 is positioned so that it presents a minimal cross-section in the direction of air flow through longitudinal member 10. Thus air flow is maximized. When in the fully closed position, the illustrated valve plate 50 preferably contacts the inside surface 18 of longitudinal member 10 to create a seal which effectively blocks the flow of air through longitudinal member 10. It is understood that valve plate 50 need not create a perfect seal against the inner surface 18, and the term "seal" should be read to include an imperfect seal as may often be formed by valve plate 50. In this exemplary embodiment, both valve plate 50 and longitudinal member 10 may be constructed of a flexible rubber material, although any material or combination of materials may be used.

Figure 8:
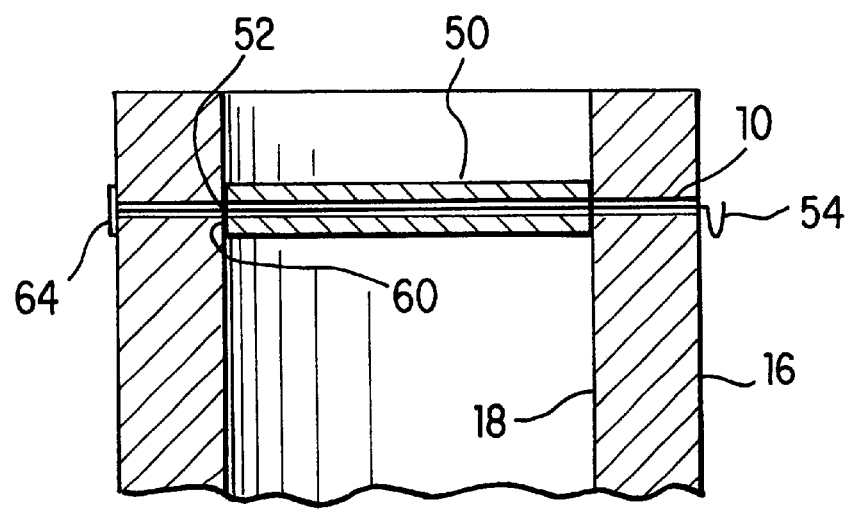
FIG. 8 is another cross sectional view of the flow control device of FIG. 5.

Valve plate 50 preferably pivots on a pin 52. Pin 52 may be inserted through valve plate 50 and through the walls of longitudinal member 10 (see FIG. 8). Pin 52 may engage valve plate 50 in frictional interference such that when the pin 52 is pivoted, valve plate 50 also pivots. Alternatively, pin 52 may be fused, glued, or otherwise rigidly attached to valve plate 50. Pin 52 preferably protrudes through the outside surface 16 of longitudinal member 10. In this manner, pin 52 may also maintain frictional interference with longitudinal member 10 such that when valve plate 50 is rotated to a desired position, it will remain in that position until further manipulated by the user. It is understood that while the illustrated embodiment shows valve plate 50 and pin 52 as distinct elements, the two could be formed integrally.

One protruding end 64 of pin 52 may be bent to prevent pin 52 from retracting through the wall of longitudinal member 10. A second protruding end of pin 52 may be shaped to form a handle 54, which may be manipulated to selectively position valve plate 50 between the fully open and fully closed positions. While handle 54 is shown integral with pin 52, handle 54 could be formed separately and attached to pin 52.

The device according to the present invention has been described with respect to two exemplary embodiments. It can be understood, however, that there are many other variations of the above-described embodiments which will be apparent to those skilled in the art, even where elements have not explicitly been designated as exemplary. For example longitudinal member 10 could be constructed integrally with an endotracheal tube, removing the need for a separate air conduit 40. It is understood that this and other modifications are within the teaching of the present invention, which is to be limited only by the claims appended hereto.

What is claimed is:

1. An endotracheal tube flow control device, comprising:
    a longitudinal member, adapted to interconnect to a trachea, having proximal and distal ends and having a bore therethrough;
    a valve mechanism disposed within the longitudinal member, the valve member being selectively and gradually positionable between a fully open position and a fully closed position;
    wherein the valve mechanism includes:
        a flange located at the distal end of the longitudinal member, the flange having a distal face and having a recess in the distal face, the recess being in fluid communication with the bore of the longitudinal member; and
        an end cap rotatably coupled to the flange, the end cap having an end face with at least one aperture therethrough, wherein the end cap is selectively and gradually rotatable between the fully open position in which the at least one aperture is in maximum fluid connection to the recess and the fully closed position in which the at least one aperture is in minimal fluid connection to the recess; and
    wherein the recess is semi-circular, extending concentrically outward from the bore of the longitudinal member.

2. An endotracheal tube flow control device, comprising:
    a longitudinal member, adapted to interconnect to a trachea, having proximal and distal ends and having a bore therethrough;
    a valve mechanism disposed within the longitudinal member, the valve member being selectively and gradually positionable between a fully open position and a fully closed position;
    wherein the valve mechanism includes:
        a flange located at the distal end of the longitudinal member, the flange having a distal face and having a recess in the distal face, the recess being in fluid communication with the bore of the longitudinal member; and
        an end cap rotatably coupled to the flange, the end cap having an end face with at least one aperture therethrough, wherein the end cap is selectively and gradually rotatable between the fully open position in which the at least one aperture is in maximum fluid connection to the recess and the fully closed position in which the at least one aperture is in minimal fluid connection to the recess; and the end cap further including:

a skirt depending from an outer edge of the end face, the skirt having an inner diameter at least as great as an outer diameter of the flange; and an inwardly protruding lip disposed on a distal edge of the skirt, the lip having an inner diameter smaller than the outer diameter of the flange;

wherein the end cap connects to the flange in a snap-fit relationship.

3. An endotracheal tube flow control device, comprising:

a longitudinal member, adapted to interconnect to a trachea, having proximal and distal ends and having a bore therethrough;

a valve mechanism disposed within the longitudinal member, the valve mechanism being selectively and gradually positionable between a fully open position and a fully closed position;

wherein the valve mechanism includes:

a flange located at the distal end of the longitudinal member, the flange having a distal face and having a recess in the distal face, the recess being in fluid communication with the bore of the longitudinal member; and an end cap rotatably coupled to the flange, the end cap having an end face with at least one aperture therethrough, wherein the end cap is selectively and gradually rotatable between the fully open position in which the at least one aperture is in maximum fluid connection to the recess and the fully closed position in which the at least one aperture is in minimal fluid connection to the recess;

an air conduit coupled to the longitudinal member; and wherein an inner surface of the air conduit frictionally engages an outer surface of the longitudinal member, and wherein a distal end of the air conduit abuts a proximal surface of the flange.

4. An endotracheal tube flow control device, comprising:

a longitudinal member, adapted to interconnect to a trachea, having proximal and distal ends and having a bore therethrough;

a valve mechanism disposed within the longitudinal member, the valve mechanism being selectively and gradually positionable between a fully open position and a fully closed position;

wherein the valve mechanism includes:

a flange located at the distal end of the longitudinal member, the flange having a distal face and having a recess in the distal face, the recess being in fluid communication with the bore of the longitudinal member; and an end cap rotatably coupled to the flange, the end cap having an end face with at least one aperture therethrough, wherein the end cap is selectively and gradually rotatable between the fully open position in which the at least one aperture is in maximum fluid connection to the recess and the fully closed position in which the at least one aperture is in minimal fluid connection to the recess;

an air conduit coupled to the longitudinal member; and wherein the air conduit is an endotracheal tube.

5. An endotracheal tube flow control device, comprising:

a longitudinal member, adapted to interconnect to a trachea, having proximal and distal ends and having a bore therethrough;

a valve mechanism disposed within the longitudinal member, the valve mechanism being selectively and gradually positionable between a fully open position and a fully closed position;

wherein the valve mechanism includes:

a valve plate rotatably disposed within the bore of the longitudinal member, the valve plate selectively and gradually rotating about a pin between the fully open position in which the valve plate presents a minimal cross-section in the direction of air flow and the fully closed position in which an edge of the valve plate forms a seal against an inner surface of the longitudinal member;

wherein first and second ends of the pin protrude through the longitudinal member.

6. The device according to claim 5, wherein the first end of the pin is bent to prevent retraction of the first end through the longitudinal member.

7. The device according to claim 5, further including a handle connected to the second end of the pin, the handle being manipulated to rotate the valve plate.

8. The device according to claim 7, wherein the handle is integral with the second end of the pin.

9. An endotracheal tube, comprising:

a longitudinal member having proximal and distal ends and having a bore therethrough, the proximal end adapted for insertion into a patient;

a valve mechanism disposed at the distal end of the longitudinal member, the valve mechanism being selectively and gradually positionable between a fully open position and a fully closed position;

wherein the valve mechanism comprises:

a flange located at the distal end of the longitudinal member, the flange having a distal face and having a recess in the distal face, the recess being in fluid communication with the bore of the longitudinal member; and an end cap rotatably coupled to the flange, the end cap having an end face with at least one aperture therethrough, wherein the end cap is selectively and gradually rotatable between the fully open position in which the at least one aperture is in maximum fluid connection to the recess and the fully closed position in which the at least one aperture is in minimal fluid connection to the recess.

10. The endotracheal tube according to claim 9, wherein the at least one aperture includes a plurality of apertures grouped on one side of the end face.

11. The endotracheal tube according to claim 9, wherein the recess is semi-circular, extending concentrically outward from the bore of the longitudinal member.

12. The endotracheal tube according to claim 9, the end cap further including:

a skirt depending from an outer edge of the end face, the skirt having an inner diameter at least as great as an outer diameter of the flange; and an inwardly protruding lip disposed on a distal edge of the skirt, the lip having an inner diameter smaller than the outer diameter of the flange;

wherein the end cap connects to the flange in a snap-fit relationship.

13. An endotracheal tube, comprising:

a longitudinal member having proximal and distal ends and having a bore therethrough, the proximal end adapted for insertion into a patient;

a valve mechanism disposed within the longitudinal member, the valve mechanism being selectively and gradually positionable between a fully open position and a fully closed position;

the valve mechanism including:

a valve plate rotatably disposed within the bore of the longitudinal member, the valve plate selectively and gradually rotating about a pin between the fully open position in which the valve plate presents a minimal cross-section in the direction of air flow and the fully closed position in which an edge of the valve plate forms a seal against an inner surface of the longitudinal member;

wherein first and second ends of the pin protrude through the longitudinal member.

14. The endotracheal tube according to claim 13, wherein the first end of the pin is bent to prevent retraction of the first end through the longitudinal member.

15. The endotracheal tube according to claim 13, further including a handle connected to the second end of the pin, the handle being manipulated to rotate the valve plate.

16. The endotracheal tube according to claim 15, wherein the handle is integral with the second end of the pin.

* * * * *